United States Patent
Patel et al.

(10) Patent No.: US 9,918,884 B2
(45) Date of Patent: Mar. 20, 2018

(54) REMOTE MONITORING OF ABSORBENT ARTICLE

(71) Applicant: Covidien LP, Mansfield, MA (US)

(72) Inventors: Harish Patel, Norfolk, MA (US);
Robert Gaines, Lake Saint Louis, MO (US); Vishal Narvekar, Mansfield, MA (US); Richard Gahan, Wrentham, MA (US)

(73) Assignee: KPR U.S., LLC, Mansfield, MA (US)

( * ) Notice: Subject to any disclaimer, the term of this patent is extended or adjusted under 35 U.S.C. 154(b) by 385 days.

(21) Appl. No.: 14/693,427

(22) Filed: Apr. 22, 2015

(65) Prior Publication Data

US 2016/0310329 A1    Oct. 27, 2016

(51) Int. Cl.
| | | |
|---|---|---|
| *G08B 21/00* | (2006.01) | |
| *A61F 13/42* | (2006.01) | |
| *A61B 5/11* | (2006.01) | |
| *A61B 5/00* | (2006.01) | |

(52) U.S. Cl.
CPC ............ *A61F 13/42* (2013.01); *A61B 5/0002* (2013.01); *A61B 5/1116* (2013.01); *A61B 5/1118* (2013.01); *A61B 5/6808* (2013.01); *A61B 2503/08* (2013.01); *A61F 2013/424* (2013.01)

(58) Field of Classification Search
CPC . A61B 2503/08; A61B 5/0002; A61B 5/1116; A61B 5/1118; A61B 5/6808
USPC ....................................... 340/573.5
See application file for complete search history.

(56) References Cited

U.S. PATENT DOCUMENTS

| 5,264,830 | A | 11/1993 | Kline et al. |
|---|---|---|---|
| 5,760,694 | A * | 6/1998 | Nissim .................... A61F 13/42 128/885 |
| 7,522,061 | B2 | 4/2009 | Rondoni et al. |
| 7,855,653 | B2 | 12/2010 | Rondoni et al. |
| 8,072,338 | B2 | 12/2011 | Rondoni et al. |
| 8,471,715 | B2 | 6/2013 | Solazzo et al. |
| 8,694,600 | B2 | 4/2014 | Gaines et al. |
| 2002/0070868 | A1 * | 6/2002 | Jeutter .................... A61F 13/42 340/604 |
| 2005/0195085 | A1 | 9/2005 | Cretu-Petra |
| 2008/0266117 | A1 * | 10/2008 | Song ....................... A61F 13/42 340/573.5 |

(Continued)

OTHER PUBLICATIONS

"XBee Gateway Family," Digi International Inc., retrieved from http://www.digi.com/pdf/ds_xbeegateway.pdf on Apr. 13, 2015, 3 pp.

*Primary Examiner* — Mark Rushing
(74) *Attorney, Agent, or Firm* — Nicole M. Creegan

(57) ABSTRACT

In one example, a sensor system of a patient monitoring system includes a voiding sensor that includes an electrical circuit configured to be transitioned from a first impedance state to a second impedance state in response to a voiding event in an absorbent region of an absorbent article worn by a patient. The sensor system also includes one or more processors configured to: determine, based on whether the impedance state of the electrical circuit is open or closed, that the voiding event has occurred; and generate, based at least in part on the occurrence of the voiding event, patient status data of the patient. The sensor system also includes a communication module configured to wirelessly transmit, via a relay module, the patient status data to a remote monitoring device that is distinct from the relay module.

20 Claims, 8 Drawing Sheets

(56) References Cited

U.S. PATENT DOCUMENTS

| | | |
|---|---|---|
| 2012/0182894 A1 | 7/2012 | Gaines et al. |
| 2012/0182927 A1 | 7/2012 | Wiesner et al. |
| 2012/0184207 A1 | 7/2012 | Gaines et al. |
| 2012/0185268 A1 | 7/2012 | Wiesner et al. |
| 2012/0268278 A1* | 10/2012 | Lewis ............ A61F 13/42 340/573.5 |
| 2014/0121473 A1* | 5/2014 | Banet ............ A61B 5/0015 600/301 |
| 2014/0152466 A1 | 6/2014 | Wiesner et al. |
| 2014/0266736 A1 | 9/2014 | Cretu-Petra |
| 2015/0080819 A1* | 3/2015 | Charna ............ A61F 13/42 604/361 |

* cited by examiner

REMOTE MONITORING OF ABSORBENT ARTICLE

TECHNICAL FIELD

The disclosure relates to remote patient monitoring.

BACKGROUND

Urinary incontinence, or an inability to control urinary function, is a common problem afflicting people of all ages, genders, and races. Various muscles, nerves, organs, and conduits within the urinary tract cooperate to collect, store and release urine. A variety of disorders may compromise urinary tract performance and contribute to incontinence. Many of the disorders may be associated with aging, injury, or illness. Some patients with urinary incontinence may wear an absorbent undergarment to absorb voided fluids (e.g., urine).

SUMMARY

In one example, a sensor system of a patient monitoring system includes a voiding sensor, one or more processors, and a communications module. In this example, the voiding sensor includes an electrical circuit configured to be transitioned from a first impedance state to a second impedance state in response to a voiding event in an absorbent region of an absorbent article worn by a patient. In this example, the electrical circuit is either open or closed in the first impedance state and the other of open or closed in the second impedance state. In this example, the one or more processors are configured to: determine, based on whether the impedance state of the electrical circuit is open or closed, that the voiding event has occurred or is present; and generate, based at least in part on the occurrence or presence of the voiding event, patient status data of the patient. In this example, the communication module is configured to wirelessly transmit, via at least one relay module, the patient status data to a remote monitoring device that is distinct from the relay module.

In some examples, the electrical circuit is open in the first impedance state and closed in the second impedance state. In some examples, the electrical circuit comprises a first electrically conductive pathway and a second electrically conductive pathway configured to conduct in response to the voiding event such that the electrical circuit closes in response to the voiding event. In some examples, the first and second electrically conductive pathways each comprise at least one of: an electrically conductive ink and an electrically conductive wire.

In some examples, the electrical circuit is closed in the first impedance state and open in the second impedance state. In some examples, the electrical circuit comprises an electrically conductive pathway that comprises an electrically conductive material configured to at least partially dissolve in response to the voiding event such that the electrical circuit opens in response to the voiding event.

In some examples, the patient status data is first patient status data, the sensor system further comprises one or more motion sensors configured to generate motion data indicative of motion of the patient, the one or more processors are further configured to: determine, based at least in part on the motion data, patient motion or posture state, and generate, based at least in part on the patient motion or posture state, second patient status data, and the communication module is further configured to wirelessly transmit, to the relay module, the second patient status data, the relay module being configured to wirelessly transmit the received second patient status data to the remote monitoring device. In some examples, the one or more processors are configured to cause the communication module to transmit the second patient status data within a predetermined time of day.

In some examples, the one or more processors are further configured to: determine, based on motion data, whether an activity level of the patient satisfies an activity level threshold, and cause the communication module to transmit, responsive to the activity level of the patient satisfying the activity level threshold, the second patient status data. In some examples, the one or more processors are further configured to cause the communication module to transmit, responsive to the posture state being a sitting posture state or a standing posture state, the second patient status data. In some examples, the one or more motion sensors comprise an accelerometer.

In some examples, the relay module comprises: a receiver configured to wirelessly receive, via a wireless relay network and from the sensor system, the patient status data; a first transmitter configured to wirelessly transmit the patient status data over an internet-accessible wireless communications network; a second transmitter configured to wirelessly transmit the patient status data to a second wireless relay module over the wireless relay network; and one or more processors coupled to the first and second transmitters, the one or more processors being configured to select one of the first transmitter or the second transmitter for transmitting the received patient status data. In some examples, the receiver is configured to wirelessly receive the patient status data over the wireless relay network from a plurality of sensor systems.

In some examples, the system further comprises the absorbent article, and the voiding sensor is configured to be attached to the absorbent article.

In another example, a method of monitoring a patient status includes transitioning, by an electrical circuit of a voiding sensor of a sensor system, from a first impedance state to a second impedance state in response to a voiding event in an absorbent region of an absorbent article worn by a patient. In this example, the electrical circuit is either open or closed in the first impedance state and the other of open or closed in the second impedance state. In this example, the method also includes determining, by one or more processors of the sensor system and based on whether the impedance state of the electrical circuit has transitioned, that the voiding event has occurred, and generating, by the one or more processors and based at least in part on the occurrence of the voiding event, patient status data of the patient. In this example, the method also includes wirelessly transmitting, by a communication module of the sensor system and via a relay module that is distinct from the sensor system, the patient status data to a remote monitoring device that is distinct from the relay module.

In some examples, the electrical circuit is open in the first impedance state and closed in the second impedance state. In some examples, the electrical circuit is closed in the first impedance state and open in the second impedance state. In some examples, the patient status data is first patient status data, the method further comprising, at the remote monitoring device, wirelessly receiving from the communication module and via the relay module, second patient status data including patient motion data that is indicative of at least one of a patient motion and patient posture state. In some examples, the method further comprises determining, based at least on the motion data, whether an activity level of the patient satisfies an activity level threshold; and wirelessly transmitting the second patient status data in response to the activity level of the patient satisfying the activity level threshold.

In another example, a computer-readable storage medium stores instructions that, when executed, cause one or more processors of a sensor system to determine, based on whether an impedance state of an electrical circuit of the sensor system has transitioned from a first impedance state to a second impedance state, that the voiding event has occurred. In this example, the electrical circuit is configured to transition from the first impedance state to the second impedance state in response to a voiding event in an absorbent region of an absorbent article worn by a patient, and the electrical circuit is either open or closed in the first impedance state and the other of open or closed in the second impedance state. In this example, the computer-readable storage medium also stores instructions that, when executed, cause the one or more processors to generate, based at least in part on the occurrence of the voiding event, patient status data of the patient. In this example, the computer-readable storage medium also stores instructions that, when executed, cause the one or more processors to cause a communication module of the sensor system to wirelessly transmit, via a relay module that is distinct from the sensor system, the patient status data to a remote monitoring device that is distinct from the relay module.

In another example, a method of monitoring a status of a patient includes receiving, by a remote monitoring device, from a sensor system, and via a relay module that is distinct from the remote monitoring device, patient status data for the patient, wherein the sensor system is configured to identify a voiding event in an absorbent region of an absorbent article and includes: a voiding sensor comprising an electrical circuit configured to be transitioned from a first impedance state to a second impedance state in response to a voiding event in an absorbent region of an absorbent article, one or more processors configured to determine, based on whether the impedance state of the electrical circuit that the voiding event has occurred, and further configured to generate, based at least in part on the second impedance state, the patient status data, and a communication module configured to wirelessly transmit, via the relay module and to the remote monitoring device, the patient status data; and in response to determining, based on the patient status data, that the patient has experienced a voiding event, outputting, by the remote monitoring device, an indication that the patient has experienced a voiding event.

In some examples, the method also includes receiving, by the remote monitoring device and via the relay module, patient status data for a plurality of respective patients, the patient status data for the plurality of patients being generated by a plurality of respective sensor systems. In some examples, the plurality of patients is a first plurality of patients, the plurality of sensor systems is a first plurality of sensor systems, the relay module is a first relay module, and the method further comprises receiving, by the remote monitoring device and via a second relay module that is distinct from the remote monitoring device and the first relay module, patient status data for a second plurality of respective patients, the patient status data for the second plurality of patients being generated by a second plurality of respective sensor systems.

In some cases, the method of monitoring a status of a patient comprises receiving, by a remote monitoring device, from a sensor system, and via a relay module that is distinct from the remote monitoring device, patient status data for the patient, wherein the sensor system is configured to identify a voiding event in an absorbent region of an absorbent article and includes: a voiding sensor comprising an electrical circuit configured to be transitioned from a first impedance state to a second impedance state in response to a voiding event in an absorbent region of an absorbent article, one or more processors configured to determine, based on whether the impedance state of the electrical circuit that the voiding event has occurred, and further configured to generate, based at least in part on the second impedance state, the patient status data, and a communication module configured to wirelessly transmit, via the relay module and to the remote monitoring device, the patient status data. The method can further comprise receiving, by the remote monitoring device and via the relay module, a plurality of patient status data for a plurality of respective patients, each of the plurality of patient status data generated by a plurality of respective sensor systems. The plurality of patients can be a first plurality of patients, wherein the plurality of sensor systems is a first plurality of sensor systems each of which is respectively associated with a patient of the first plurality of patients, and wherein the relay module is a first relay module, and wherein the method further comprises receiving, by the remote monitoring device and via a second relay module that is distinct from the remote monitoring device and the first relay module, patient status data for a second plurality of respective patients, the patient status data for the second plurality of patients being generated by a second plurality of respective sensor systems. The method can further comprise providing, by the remote monitoring device, an indication that the patient has experienced a voiding event.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

Figure 1:
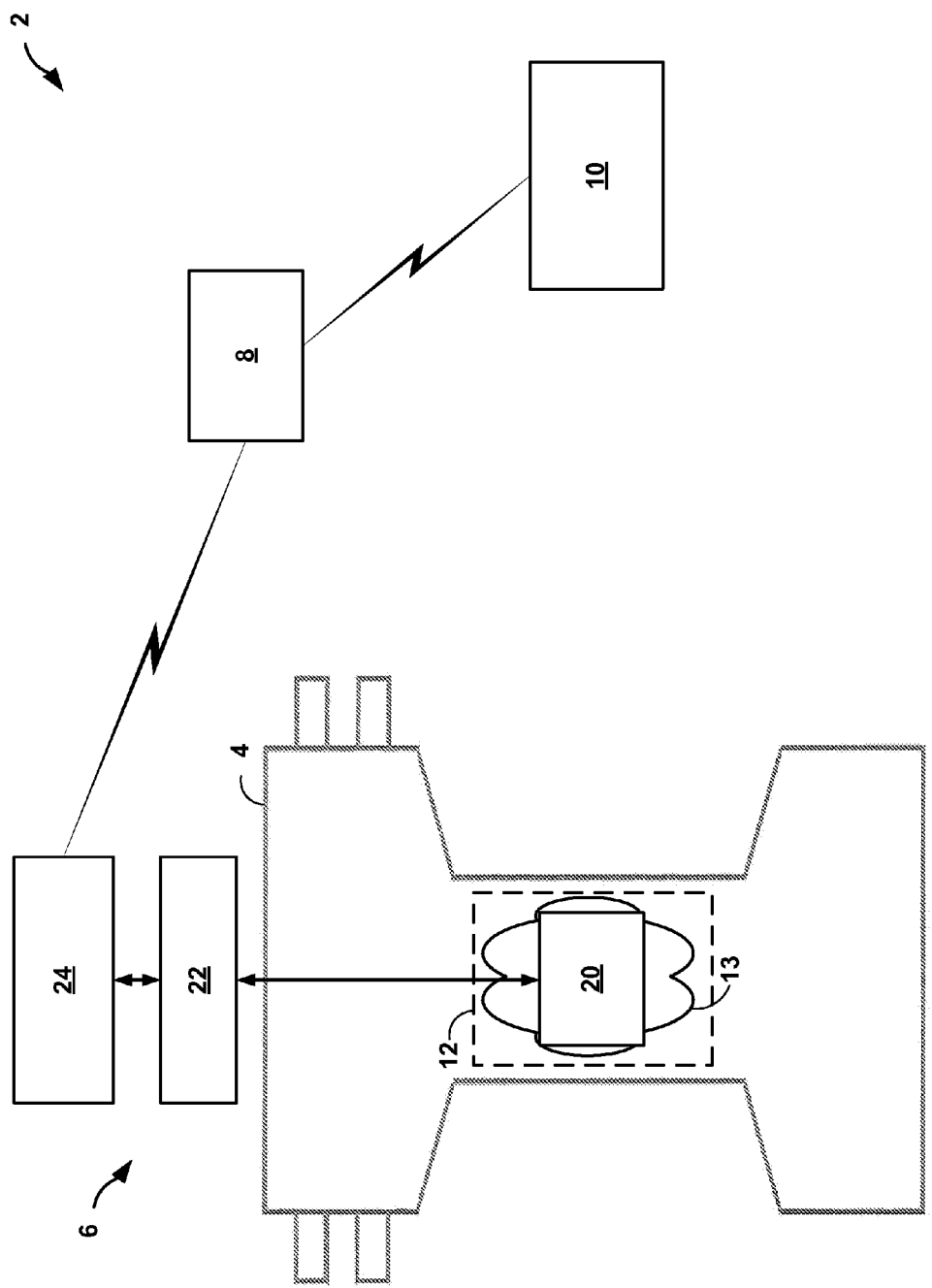
FIG. 1 illustrates an example patient monitoring system including a sensor system configured to detect a voiding event of a patient, in accordance with one or more techniques of this disclosure.

Urinary incontinence is a condition that affects the quality of life and health of many people. Some patients with urinary incontinence may wear an absorbent article (e.g., undergarment, briefs, diaper, and the like) to absorb voided fluids (e.g., urine). In some examples, it may be desirable to detect urinary voiding events in patients wearing absorbent articles. For example, it may be important to ensure that the absorbent article is changed in a timely manner after a voiding event. In some cases, if an absorbent article is not changed in a timely manner after a voiding event, then a patient may develop skin irritation, bedsores, or other undesirable conditions. However, some patients who wear absorbent articles do not or cannot change themselves or inform their caretakers (e.g., nurses, family members, and the like) that a voiding event has occurred. As such, it may be desirable for a caretaker to be alerted to the occurrence of a voiding event of a patient wearing an absorbent article.

In accordance with one or more techniques of this disclosure, a patient monitoring system may include a sensor system and a remote monitoring device. The sensor system may include a voiding sensor configured to detect a voiding event in an absorbent article worn by a patient and a communication module configured to wirelessly transmit an indication of the voiding event to the remote monitoring device. In this way, the sensor system may enable a caretaker to determine an occurrence of a patient's voiding event without being directly informed by the patient. Some example patient monitoring systems are described by Gaines et al. (U.S. Patent Publication No. 2012/0182894 A1), Gaines et al. (U.S. Patent Publication No. 2012/0184207 A1), Wiesner et al. (U.S. Patent Publication No. 2014/0152466 A1), Wiesner et al. (U.S. Patent Publication No. 2012/0185268 A1), Wiesner et al. (U.S. Patent Publication No. 2012/0182927 A1), and Gaines et al. (U.S. Pat. No. 8,694,600 B2), the entirety of which are herein incorporated by reference for all purposes.

In some scenarios, a single caretaker or a limited number of caretakers may be responsible for a plurality of patients wearing absorbent articles. The patient monitoring systems described herein may help the one or more caretakers monitor a plurality of patients in an efficient manner.

In some examples, it may not be desirable to tether the patient (e.g., to an outlet) with power supply lines. As such, the sensor system may include a battery to power the components of the sensor system. The amount of power a battery provides may be proportional to the physical size of the battery and the cost of the battery. As the sensor system may be attached to the absorbent article worn by the patient, it may be desirable to minimize the physical size of the battery. In order to minimize the physical size of the battery without significantly increasing the cost of the battery or significantly decreasing the amount of time the battery may power the sensor system, it may be desirable to minimize the amount of power consumed by the sensor system. As one example, it may be desirable to minimize the amount of power consumed by the sensor system when detecting voiding events. As another example, it may be desirable to minimize the amount of power consumed by the sensor system when transmitting indications of voiding events to a central monitoring station.

The voiding sensor may be configured to detect voiding events in a plurality of ways. For instance, the voiding sensor may include an electrical circuit configured to be transitioned from a first impedance state to a second impedance state in response to a voiding event. As one example, where the electrical circuit is closed in the first impedance state and open in the second impedance state, the presence of voiding fluids (e.g., urine) may cause the electrical circuit to transition from closed to open. For instance, the electrical circuit may include an electrically conductive material configured to at least partially dissolve in the presence of voiding fluids (which may cause the electrical circuit to transition from closed to open). In this way, as electrical circuit transitions from closed to open in response to the voiding event, the sensor system would be able to determine that the sensor is working prior to the occurrence of the voiding event, such as by periodically transmitting an electrical signal through the electrical circuit.

As another example, the electrical circuit may be open in the first impedance state and closed in the second impedance state, the presence of voiding fluids (e.g., urine) may cause the electrical circuit to transition from open to closed. For instance, the electrical circuit may include a material configured to become electrically conductive in the presence of voiding fluids (which may cause the electrical circuit to transition from open to closed). In this way, as current only flows through the electrical circuit in response to the voiding event, the amount of power consumed by the sensor system when detecting voiding events may be reduced.

In some examples, it may be desirable for a single caretaker or a limited number of caretakers (less than the number of patients) to monitor a plurality of patients wearing absorbent articles. As such, in accordance with one or more techniques of this disclosure, as opposed to requiring that a caretaker monitor each patient with a separate monitoring device, a single remote monitoring device may be capable of monitoring a plurality of patients. For example, a remote monitoring device may be configured to receive indications of voiding events from a plurality of sensor systems, each being associated with a respective patient, and notify a caretaker which patients have experienced a voiding event (and are in need of attention, such as changing of the absorbent article).

In addition, in some examples, the remote monitoring device may be configured to receive patient data from one or more other medical devices in addition to the sensor systems including voiding sensors described herein. For example, the remote monitoring device may be configured to receive data from medical devices that deliver therapy (e.g., drug delivery pumps, electrical stimulation devices, and the like), wireless feeding pumps, and sensor systems that monitor other patient parameters (e.g., heart rate, respiration rate, blood oxygen level, and the like). In some examples, the remote monitoring device may be configured to receive this data from a plurality of patients, e.g., via one or more relay modules. In this way, the remote monitoring device may aggregate patient data from a plurality of patients and a plurality of patient systems, and, therefore, may provide a single interface by which a clinician or other caretaker may efficiently monitor one or more patients. In some cases, a plurality of relay modules is utilized to deliver the data to the remote monitoring device. For example, at least a portion of data from a patient is transmitted and received at a first relay module which transmits to a second relay module, typically wirelessly, which in turn transmits the at least a portion of the data to the remote monitoring device. If the first relay module fails to receive confirmation or acknowledgement of the receipt of the data by the remote monitoring device or fails to establish communication with the remote monitoring device, the first relay module can wirelessly transmit the data to the second relay module, e.g., within a predetermined receipt confirmation period. The second relay module can then attempt to transmit the data to the remote monitoring device. If the second relay module fails to receive confirmation or acknowledgement of the receipt of the data by the remote monitoring device or fails to establish communication with the remote monitoring device, e.g., within a similar receipt confirmation period, the second relay module can wirelessly transmit the data to a third relay module. In turn, the third relay module can transmit the data to the remote monitoring device. In some examples, the first relay module and each further relay module are in proximate arrangement with each other and within a first separation distance, and the remote monitoring device is distant from any and each of the first and each further relay module at second separation distance that is greater than the first separation distance. For example, each of the relay modules can be proximate each other and be on the same floor or within two floors of a building. Thus, in some configurations, the first separation distance can be with a volume of a single structure or building. The remote monitoring device can be disposed at a different structure or building, at second separation distance from the first building. Thus, the second separation distance can be at least twice the magnitude of the first separation distance.

In some examples, in addition to notifying a caretaker via a remote monitoring device, a patient monitoring system may further notify one or more other parties of the occurrence of a voiding event. For instance, a patient monitoring system may send a message (e.g., a text message, or an e-mail message) to a family member of a patient when the patient experiences a voiding event. In some examples, the patient monitoring system may further send a follow-up message to the family member once the patient has been changed. In this way, a patient monitoring system may allow family member to ensure that the patient is being adequately cared for by the caregiver.

In some examples, it may be desirable for the patient to be physically separated from the remote monitoring device. For example, to continue with the example in which a single caretaker or a limited number of caretakers monitor a plurality of patients, it may be desirable for the single remote monitoring device to be located at a central location (e.g., a nurse's station) and for the patients (and their absorbent articles) to be located in their respective rooms. To enable this separation, the communication module may communicate (e.g., transmit the indication) using a high-power, transmitter, such as a conventional cellular network transmitter that transmits on frequencies in the 800-4000 megahertz (MHz) range. For example, the communication module may transmit the indication to a cell site which may forward the indication to the remote monitoring device (e.g., via the internet or the public switched telephone network). In this way, the communication module (and the patient) may be physically separated from the remote monitoring device.

However, in some examples, it may not be desirable for the communication module to use a high-power transmitter. For example, contrary to the desire to minimize the amount of power consumed by the sensor system when transmitting indications of voiding events, high-power transmitters, such as conventional cellular network transmitters, may consume a large amount of power, which may shorten the amount of time a battery may power the sensor system and/or require a larger/more expensive battery. Additionally, including a high-power transmitter in a sensor system may increase a size of the sensor system and/or increase a cost of the sensor system. As such, it may be desirable for a sensor system to communicate with a remote monitoring device without using a high-power transmitter while still allowing the patient to be physically separated from the remote monitoring device.

In accordance with one or more techniques of this disclosure, in addition to the sensor system and the remote monitoring device, the patient monitoring system may include a relay module configured to wirelessly receive indications of voiding events from a sensor system and wirelessly transmit the indication of the voiding events to the remote monitoring device. For example, a low-power transmitter of the sensor system (e.g., a ZigBee or Wi-Fi transmitter) may transmit an indication of a voiding event to the relay module, which may wirelessly transmit the indication to the remote monitoring device. In this way, a sensor system may consume a minimal amount of power when communicating with a remote monitoring device while still allowing the patient to be physically separated from the remote monitoring device. In some examples, the relay module is distinct from the remote monitoring device, e.g., physically separate from and, in some cases, remotely located from the remote monitoring device.

As discussed above, it may be desirable for the sensor system to use as little power as possible when transmitting indications of voiding events. By contrast, the amount of power consumed by the relay module to when transmitting indications of voiding events to the remote monitoring device may be of less consequence due to the manner in which the relay module is configured, as described below. As such, in some examples, the relay module may be configured to consume more power when transmitting indications of voiding events to the remote monitoring device than the sensor system is configured to use when transmitting indications of voiding events to the relay module. In other examples, the relay module may be configured to consume the same or less power when transmitting indications of voiding events to the remote monitoring device than the sensor system is configured to use when transmitting indications of voiding events to the relay module.

The relay module may receive power from either a conventional outlet or a battery. Where the relay module receives power from a conventional outlet, the amount of power consumed by the relay module is of less consequence than the amount of power consumed by the sensor system because, as opposed to a battery, the conventional outlet does not become depleted. Where the relay module receives power from a battery, the amount of power consumed by the relay module is of less consequence than the amount of power consumed by the sensor system because the relay module may include a larger battery than the sensor system (e.g., as it is not worn by a patient).

In some examples, it may not be desirable to completely replace the sensor system every time a patient is changed. As such, in some examples, while the absorbent article may be considered to be disposable (i.e., completely replaced after each voiding event), the sensor system may be considered to be semi-disposable. For instance, the sensor system may be replaced after a particular number of changes (e.g., 10, 100, 500, 1000, and the like) or when the battery is depleted.

In some examples, some patients who wear absorbent articles may still use conventional bathrooms to void. When using conventional bathrooms, some of such patients may still require assistance from caretakers (i.e., to prevent injuries due to falling). However, some patients do not request assistance (e.g., due to embarrassment, feelings of independence, and/or stubbornness). As such, it may be desirable for a caretaker to be notified that a patient is attempting to use a conventional bathroom.

In accordance with one or more techniques of this disclosure, in addition to notifying a caretaker of the occurrence of voiding events, a patient monitoring system may further be configured to notify a caretaker that a patient may be attempting to get out of bed or is walking, e.g., to use a conventional bathroom. For instance, the sensor system may include one or more motion sensors (e.g., accelerometers, bonded piezoelectric crystals, mercury switches, or gyros) that generate a signal indication of patient motion and/or patient posture state. In response to detecting a motion sensor signal indicative of patient motion and/or a posture state that indicates that the patient is in a posture state or is moving in a manner consistent with the posture state or motion, respectively, associated with getting out of bed or is walking or attempting to walk, the communication module of the sensor system may transmit an alert to the remote monitoring device using techniques similar to transmitting the indication of the voiding event. For instance, the communication module may transmit the alert to the relay module which may transmit the alert to the remote monitoring device. In this way, the sensor system may notify a caretaker that a patient may be attempting to get out of bed, e.g., to use a conventional bathroom, such that the caretaker may assist the patient, which may prevent injuries due to falling.

FIG. 1 illustrates an example patient monitoring system including a sensor system configured to detect a voiding event of a patient, in accordance with one or more techniques of this disclosure. As shown in FIG. 1, patient monitoring system 2 includes absorbent article 4, sensor system 6, relay module 8, and remote monitoring device 10. Patient monitoring system 2 may be used in a plurality of settings, such as a home health setting (e.g., where the patient is living at home), a hospital setting, and/or a long-term care setting.

In some examples, absorbent article 4 may be configured to be worn by a patient (e.g., between regular articles of clothing and the skin of the patient). Absorbent article 4 may include absorbent region 12 that may be positioned near the opening of the patient's urethra (not shown) and may be configured to absorb voiding fluid. Absorbent article 4 may be alternately referred to as a diaper, brief, or an undergarment.

Absorbent region 12 may be shaped to catch and retain any urine that is voided from the patient. In the example shown in FIG. 1, the shape of absorbent region 12 allows at least a portion of the absorbent region to be placed adjacent to the opening of the urethra in either a male or female patient. Absorbent region 12 allows the urine to spread throughout the region, which distributes the fluid in the region and attempts to reduce the amount of wetness against the skin of the patient. In some embodiments, absorbent region 12 may distribute fluid such that voiding sensor 20 comes into contact with a portion of the fluid. Absorbent region 12 may be constructed of cotton, cellulose, a hydrogel, some other hydrophilic material that retains urine, and can have absorbent or superabsorbent properties.

In some examples, patient monitoring system 2 may include sensor system 6, which may be configured to detect that a voiding event has occurred and wirelessly transmit an indication of the voiding event. Sensor system 6 may be configured to be attached to absorbent article 4. For instance, sensor system 6 may be encased in a housing which may be attached to absorbent article 4 (e.g., via a mechanical clip, Velcro, adhesive, or the like) or integrated in absorbent article 4 (e.g., in a pouch of absorbent article 4). In some examples, sensor system 6 may include a battery (not shown) to power the components of sensor system 6. As illustrated in FIG. 1, sensor system 6 may include voiding sensor 20, one or more processors 22 (collectively, "processors 22"), and communication module 24. Further details of one example of sensor system 6 are discussed below with reference to FIG. 2.

Sensor system 6, in some examples, may include voiding sensor 20, which may be configured to detect that a voiding event has occurred. For instance, voiding sensor 20 may be configured to generate at least one signal representative of a voiding event in absorbent region 12 of absorbent article 4. In some examples, voiding sensor 20 may include an electrical circuit configured to generate the at least one signal by transitioning from a first impedance state to a second impedance state in response to a voiding event in absorbent region 12 of absorbent article 4. In some examples, the electrical circuit may be closed in the first impedance state and open in the second impedance state and configured to transition from closed to open in response to the presence of voiding fluid in absorbent region 12. In other examples, the electrical circuit may be open in the first impedance state and closed in the second impedance state and configured to transition from open to closed in response to the presence of voiding fluid in absorbent region 12. Voiding sensor 20 may output the at least one signal to one or more other components of sensor system 6, such as one or more of processors 22.

Sensor system 6, in some examples, may include processors 22, which may be configured to implement functionality and/or process instructions for execution within sensor system 6. For instance, processors 22 may be configured to determine, based on the at least one signal generated by voiding sensor 20 (e.g., indicative of whether the impedance state of the electrical circuit is open or closed), that a voiding event has occurred. Processors 22 may be configured to generate, based at least in part on the occurrence of the voiding event, patient status data of the patient. The patient status data may be, for example, a signal that indicates a voiding event has occurred. In some examples, the patient status data may include additional information, such as one or more of: a timestamp that indicates the time at which processors 22 detected the voiding event, the patient's name or other patient identifier, the patient room number, and the like.

In some examples, processors 22 may output the patient status data to one or more components of sensor system 6. For instance, processors 22 may output the patient status data to communication module 24 to cause communication module 24 to transmit the patient status data to a remote monitoring device, such as remote monitoring device 10, via a relay module, such as relay module 8. Examples of processors 22 may include, any one or more of a microprocessor, a controller, a digital signal processor (DSP), an application specific integrated circuit (ASIC), a field-programmable gate array (FPGA), or equivalent discrete or integrated logic circuitry.

Sensor system 6, in some examples, may include communication module 24, which may be configured to wirelessly transmit data to one or more external devices. For example, communication module 24 may transmit patient status data (e.g., an indication of a voiding event) to relay module 8. Communication module 24 may be a radio frequency transceiver, or any other type of device that can wirelessly send and receive information. Examples of communication module 24 include, but are not limited to, Bluetooth, ZigBee, and/or Wi-Fi radios.

In some examples, patient monitoring system 2 may include relay module 8, which may be configured to wirelessly receive data from an external device and wirelessly transmit the received data to another external device. For instance, relay module 8 may relay data from sensor system 6 to remote monitoring device 10. In some examples, relay module 8 may be configured to wirelessly receive data from a plurality of external devices, such as a plurality of sensor systems similar to sensor system 6, and wirelessly transmit the received data to a single external device, such as remote monitoring device 10. Further details of one example of relay module 8 are discussed below with reference to FIG. 3.

In some examples, patient monitoring system 2 may include remote monitoring device 10, which may be configured to enable a caregiver to monitor one or more patients. For instance, remote monitoring device 10 may be configured to notify a caregiver of the presence or occurrence of a voiding event. Further details of one example of remote monitoring device 10 are discussed below with reference to FIG. 4.

In operation, a patient may wear absorbent article 4 and sensor system 6 may be attached to absorbent article 4. The patient may experience a voiding event. For instance, the patient may emit voiding fluid 13 (e.g., urine) into absorbent region 12 of absorbent article 4. Voiding sensor 20 may generate one or more signals in response to the voiding event. For instance, an electrical circuit of voiding sensor 20 may transition from a first impedance state (i.e., open or closed) to a second impedance state (e.g., the opposite of the first impedance state, closed or open) in response to the voiding event.

Processors 22 may determine, based on the one or more signals generated by voiding sensor 20, whether the voiding event has occurred. As one example, where the first impedance state is open, processors 22 may determine that the voiding event has occurred when the impedance state transitions to closed or remains in a closed state. As another example, where the first impedance state is closed, processors 22 may determine that the voiding event has occurred when the impedance state transitions to open or remains in an open state.

Processors 22 may generate, based at least in part on the occurrence of the voiding event, patient status data for the patient. For instance, processors 22 may generate patient status data that indicates that the patient has experienced a voiding event. Processors 22 may output the patient status data to communication module 24 which may wirelessly transmit the patient status data to one or more remote monitoring device 10 via relay module 8. For instance, processors 22 may cause communication module 24 to transmit the patient status data to relay module 8 using ZigBee protocol.

Relay module 8 may receive the patient status data from communication module 24 and transmit the patient status data to remote monitoring device 10. In some examples, relay module 8 may transmit the patient status data to remote monitoring device 10 using the same protocol as communication module 24. For instance, relay module 8 may transmit the patient status data using ZigBee. In some examples, relay module 8 may transmit the patient status data to remote monitoring device 10 using a different protocol than communication module 24. For instance, relay module 8 may transmit the patient status data using Wi-Fi or a hardwired communication protocol.

Remote monitoring device 10 may receive the patient status data from relay module 8 and generate and present one or more notifications based on the received patient status data. For instance, where the patient status data indicates that the patient (i.e., the patient wearing absorbent article 4) has experienced a voiding event, remote monitoring device 10 may present one or more notifications (e.g., visual, audible, somatosensory, or any combinations thereof) to alert a caregiver that the patient has experienced the voiding event and needs attention, e.g., absorbent article 4 may need to be changed. In this way, sensor system 6 may consume a minimal amount of power when communicating with remote monitoring device 10 while still allowing the patient to be physically separated from remote monitoring device 10.

Figure 2:
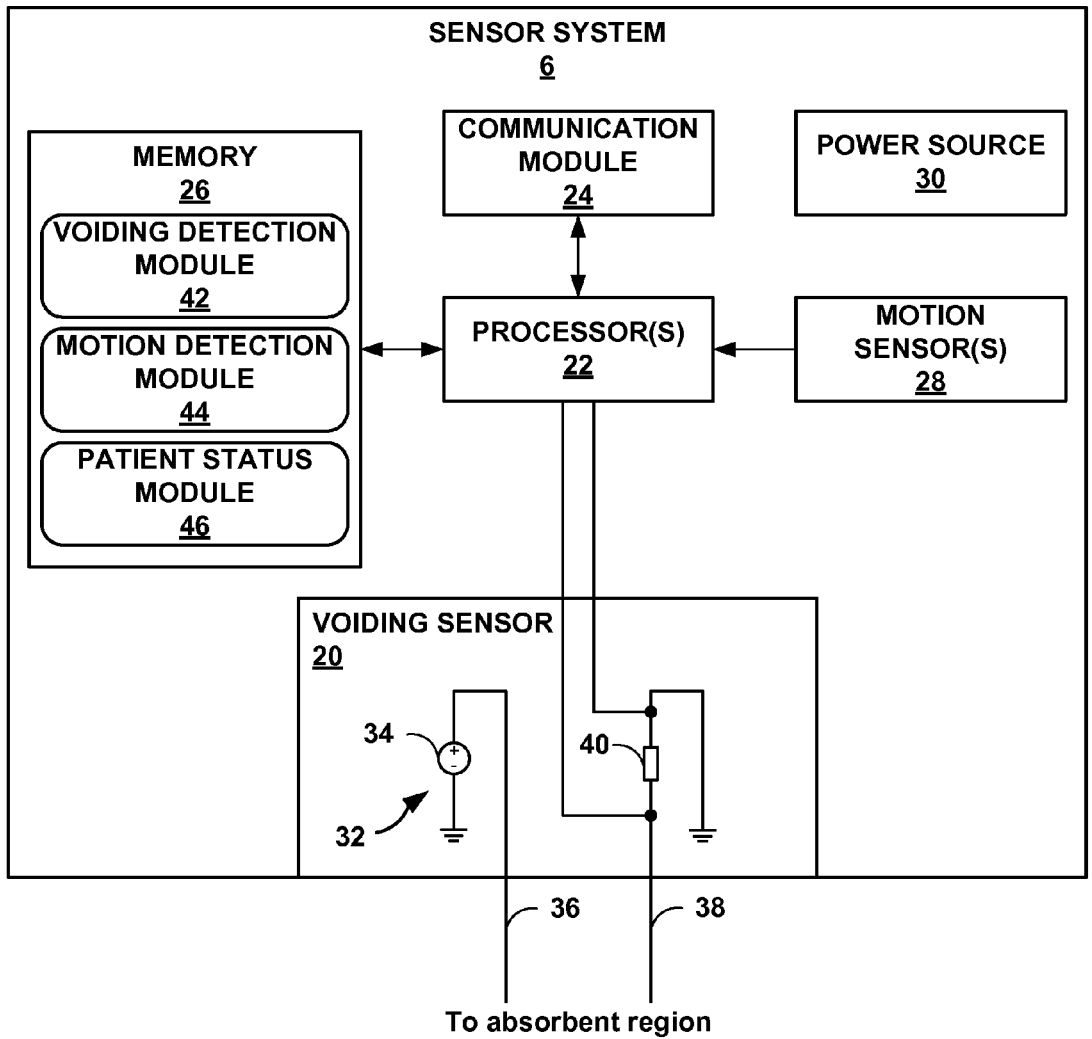
FIG. 2 is a functional block diagram illustrating components of one example of the sensor system of FIG. 1

FIG. 2 is a functional block diagram illustrating components of one example of sensor system 6 of FIG. 1. As illustrated in FIG. 2, sensor system 6 may include one or more processors 22, communication module 24, memory 26, one or more motion sensors 28, and power source 30. Processors 22 may control communication module 24, and may store and retrieve information and instructions to and from memory 26. Processors 22 may comprise any combination of one or more processors including one or more microprocessors, DSPs, ASICs, FPGAs, or other equivalent integrated or discrete logic circuitry. Accordingly, processors 22 may include any suitable structure, whether in hardware, software, firmware, or any combination thereof, to perform the functions ascribed herein to processors 22.

Voiding sensor 20 which may be configured to detect that a voiding event has occurred. As illustrated in FIG. 2, voiding sensor 20 may include electric circuit 32, which may be configured to be transitioned from a first impedance state to a second impedance state in response to a voiding event in an absorbent region of an absorbent article, such as absorbent region 12 of absorbent article 4. As shown in the example of FIG. 2, electric circuit 32 may include voltage source 34, first electrically conductive pathway 36, second electrically conductive pathway 38, and resistor 40. In other example, electric circuit 32 may include additional components or not include some of the components shown in FIG. 2. For example, one or both of first electrically conductive pathway 36 and second electrically conductive pathway 38 may be connectors configured to couple to respective electrically conductive pathways integrated into an absorbent article, such as absorbent article 4 of FIG. 1. For example, the electrically conductive pathways integrated into absorbent article 4 may be positioned in any suitable location that is in fluid communication with absorbent region 12, such as between a back sheet or top sheet and an absorbent layer, into the absorbent layer, or between an acquisition layer and an absorbent layer.

In some examples, all or part of electric circuit 32 may be part of an absorbent article, and may, for example, be disposed when the absorbent article is disposed. In some examples, electrically conductive pathways 36, 38, the electrically conductive pathways integrated into an absorbent article may be formed from any suitable material, such as copper or aluminum.

In some examples, sensor system 6 may include one or more motion sensors 28 (referred to herein as "motion sensors 28"), which may be configured to generate motion data corresponding to movements and/or orientations of the patient (i.e., which is wearing an absorbent article to which sensor system 6 is attached). Examples of one or more of motion sensors 28 may include one or more accelerometers, one or more gyroscopes, or any other sensor capable of generating motion data.

Memory 26, as well as other memories described herein, may include any volatile or non-volatile media, such as a random access memory (RAM), read only memory (ROM), non-volatile RAM (NVRAM), electrically erasable programmable ROM (EEPROM), flash memory, and the like. Memory 26 may store computer-readable instructions that, when executed by processors 22, cause sensor system 6 to perform various functions described herein. In the example shown in FIG. 2, memory 26 may store voiding detection module 42, motion detection module 44, and patient status module 46, e.g., in separate memories within memory 26 or separate areas within memory 26.

Voiding detection module 42 may be executable by processors 22 to determine whether a voiding event has occurred. In some examples, voiding detection module 42 may determine whether a voiding event has occurred based on one or more signals generated by voiding sensors 20. For instance, voiding detection module 42 may determine whether a voiding event has occurred based on an impedance state of electrical circuit 32 of voiding sensor 20.

Motion detection module 44 may be executable by processors 22 to determine motion and/or posture state of a patient. In some examples, motion detection module 44 may determine motion and/or posture state of a patient based on motion data received from one or more of motion sensors 28. Motion detection module 44 may determine motion and/or posture state of a patient using any suitable technique, such as by template matching or using a technique described in U.S. Pat. No. 8,175,720 to Skelton et al. or in U.S. Pat. No. 8,032,229 to Gerber et al. with respect to determining a patient activity level (indicative of patient motion) and patient posture state. In some examples, motion detection module 44 associates a signal generated by a motion sensors 28 with a particular patient posture, such as sitting, recumbent, upright, and so forth, or a particular patient activity, such as walking.

Patient status module 46 may be executable by processors 22 to generate patient status data. In some examples, patient status module 46 may generate patient status data based on an occurrence of a voiding event. In some examples, patient status module 46 may generate patient status data based on a determined motion and/or posture state of a patient. Thus, in some examples, the patient status data indicates the occurrence of a voiding event, patient motion, or a particular patient posture state. Patient status module 46 may cause communication module 24 to output the generated patient status data to one or more external devices. For instance, patient status module 46 may cause communication module 24 to output generated patient status data to a relay module, such as relay module 8 of FIG. 1, for forwarding to a remote monitoring device, such as remote monitoring device 10 of FIG. 1. In some cases, communication module 24 sends the generated data, e.g., patient status data, periodically according to, for example, a predetermined schedule. Thus, communication module 24 may asynchronously send data to the remote monitoring device.

Power source 30 delivers operating power to various components of sensor system 6. Power source 30 may include a small rechargeable or non-rechargeable battery and a power generation circuit to produce the operating power. In some examples, power requirements may be small enough to allow sensor system 6 to utilize patient motion and implement a kinetic energy-scavenging device to trickle charge a rechargeable battery. In other examples, traditional batteries may be used for a limited period of time.

Figure 3:
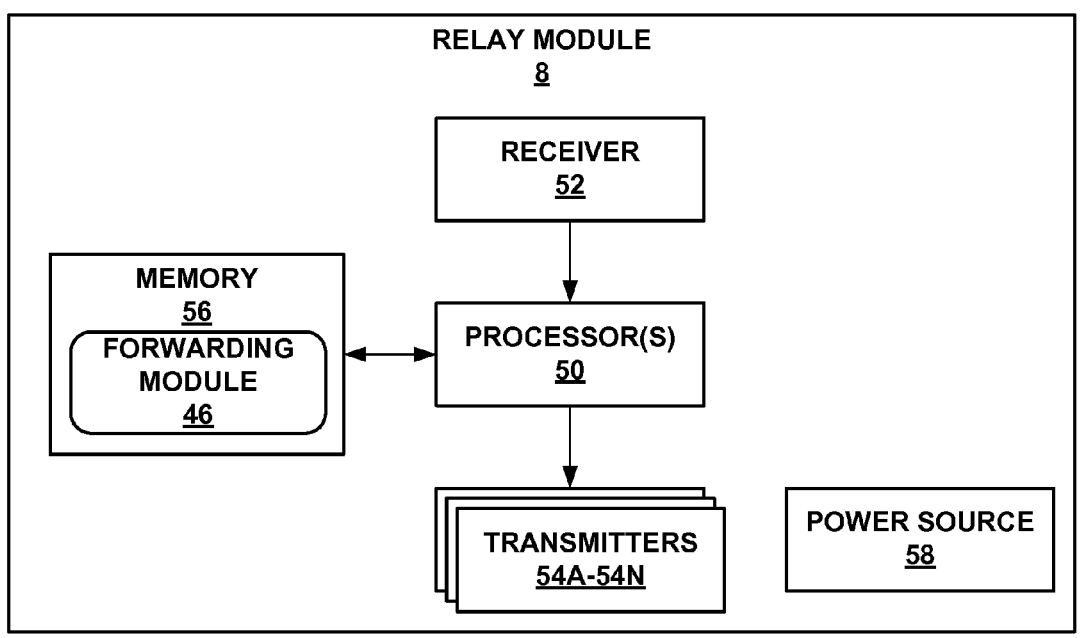
FIG. 3 is a functional block diagram illustrating components of one example of the relay module of FIG. 1.

FIG. 3 is a functional block diagram illustrating components of one example of relay module 8 of FIG. 1. As illustrated in FIG. 3, relay module 8 may include one or more processors 50, receiver 52, one or more transmitters 54A-54N (collectively, "transmitters 54"), memory 56, and power source 58. Processor 50 may control receiver 52 and transmitters 54, and may store and retrieve information and instructions to and from memory 56. Processors 50 may comprise any combination of one or more processors including one or more microprocessors, DSPs, ASICs, FPGAs, or other equivalent integrated or discrete logic circuitry. Accordingly, processors 50 may include any suitable structure, whether in hardware, software, firmware, or any combination thereof, to perform the functions ascribed herein to processors 50.

Receiver 52 may be configured to receive data from one or more external devices. For instance, receiver 52 may be configured to receive patient status data from one or more sensor systems, such as one or more of sensor system 6. In some examples, receiver 52 may also be configured to receive data from systems/devices different than sensor system 6, such as one or more wireless feeding pumps. Examples of receiver 52 include, but are not limited to, ZigBee receivers, Wi-Fi receivers, and any other receiver capable of receiving low-power transmissions. Receiver 52 may provide received data to one or more other components of relay module 8, such as processors 50.

Transmitters 54 may be configured to transmit data to one or more external devices. For instance, transmitters 54 may be controllable by processors 50 to transmit data to a remote monitoring device, such as remote monitoring device 10 of FIG. 1. In some examples, transmitters 54 may include any combination of wired and wireless transmitters. Examples of transmitters 54 include, but are not limited to, Wi-Fi transmitters, ZigBee transmitters, Ethernet transmitters, Cellular transmitters, and any other transmitter capable of transmitting data.

Memory 56, as well as other memories described herein, may include any volatile or non-volatile media, such as a RAM, ROM, NVRAM, EEPROM, flash memory, and the like. Memory 56 may store computer-readable instructions that, when executed by processors 50, cause relay module 8 to perform various functions described herein. In the example shown in FIG. 3, memory 56 may store data and instructions for forwarding module 46.

Forwarding module 46 may be executable by processors 50 to receive data from receiver 52 and cause one or more of transmitters 54 to forward the received data to one or more external devices. For instance, forwarding module 50 may receive, via receiver 54 patient status data from a sensor system and cause one or more of transmitters 54 to transmit the received patient status data to a remote monitoring device.

Power source 58 delivers operating power to various components of relay module 8. In some examples, power source 58 may include a plug configured to connect to a conventional outlet (e.g., a 120 volt, 220 volt mains outlet) and or circuitry to receive power from another device, such as via power over Ethernet (PoE). In some examples, power source 58 may also include a rechargeable or non-rechargeable battery and a power generation circuit to produce the operating power. This may enable power source 58 to continue to provide power to relay module 8 in the event of a power loss in the conventional outlet.

Figure 4:
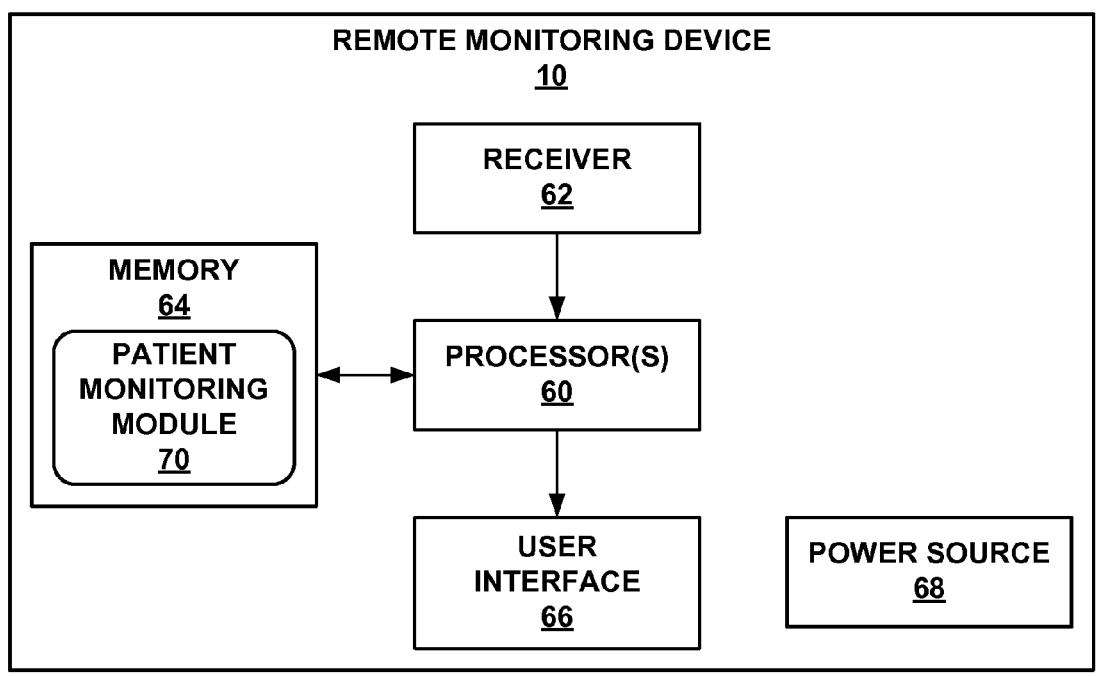
FIG. 4 is a functional block diagram illustrating components of one example of the remote monitoring device of FIG. 1.

FIG. 4 is a functional block diagram illustrating components of one example of remote monitoring device 10 of FIG. 1. Examples of remote monitoring device 10 include, but are not limited to, laptops, tablets, smartphones, servers, wearable devices (e.g., smartwatches), and any other device capable of receiving data and outputting a notification. As illustrated in FIG. 4, remote monitoring device 10 may include one or more processors 60, receiver 62, memory 64, user interface (UI) 66, and power source 68. Processor 60 may control receiver 62 and UI 66, and may store and retrieve information and instructions to and from memory 64. Processors 60 may comprise any combination of one or more processors including one or more microprocessors, DSPs, ASICs, FPGAs, or other equivalent integrated or discrete logic circuitry. Accordingly, processors 60 may include any suitable structure, whether in hardware, software, firmware, or any combination thereof, to perform the functions ascribed herein to processors 60.

Receiver 52 may be configured to receive data from one or more external devices. For instance, receiver 52 may be configured to receive patient status data from one or more relay devices, such as one or more of relay device 8. Examples of receiver 62 include, but are not limited to, ZigBee receivers, Wi-Fi receivers, Ethernet receivers, Cellular receivers, and any other receiver capable of receiving transmissions. Receiver 62 may provide received data to one or more other components of remote monitoring device 10, such as processors 60.

User interface 66 may include a display (not shown), such as a LCD or LED display or other type of screen, with which processor 60 may present information related to the patient status data (e.g., a notification that a particular patient may need attention, an indication of the occurrence of a voiding event for a particular patient, an indication of a particular patient motion or posture state, or any combination thereof). In addition, user interface 66 may include an input mechanism to receive input from the user. The input mechanisms may include, for example, any one or more of buttons, a keypad (e.g., an alphanumeric keypad), a peripheral pointing device, a touch screen, or another input mechanism that allows the user to navigate through user interfaces presented by processor 60 and provide input. In other examples, user interface 66 also includes audio circuitry for providing audible notifications, instructions or other sounds, receiving voice commands, or both.

Memory 64, as well as other memories described herein, may include any volatile or non-volatile media, such as a RAM, ROM, NVRAM, EEPROM, flash memory, and the like. Memory 64 may store computer-readable instructions that, when executed by processors 60, cause remote monitoring device 10 to perform various functions described herein. In the example shown in FIG. 4, memory 64 may store patient monitoring module 70.

Patient monitoring module 70 may be executable by processors 60 to enable a caregiver to monitor the status of one or more patients. For instance, patient monitoring module 70 may cause UI 66 to display information indicative of the status of one or more patients, as determined based on patient status information received from one or more sensor systems 6. As one example, patient monitoring module 70 may cause UI 66 to display a notification that a patient has experienced a voiding event. In some examples, patient monitoring module 70 may include recordkeeping functionality. For instance, patient monitoring module 70 may record the time at which a patient experienced a voiding event and the time at which the caregiver changed absorbent article of the patient. As another example, patient monitoring module 70 may cause UI 66 to display a notification that a patient has gotten out of bed or is attempting to get out of bed. Such a notice may provide a caretaker with advance notice for providing relatively timely aid to the patient, which may help prevent a patient fall, provide relatively timely changing of a patient's absorbent article, and the like.

Figure 5:
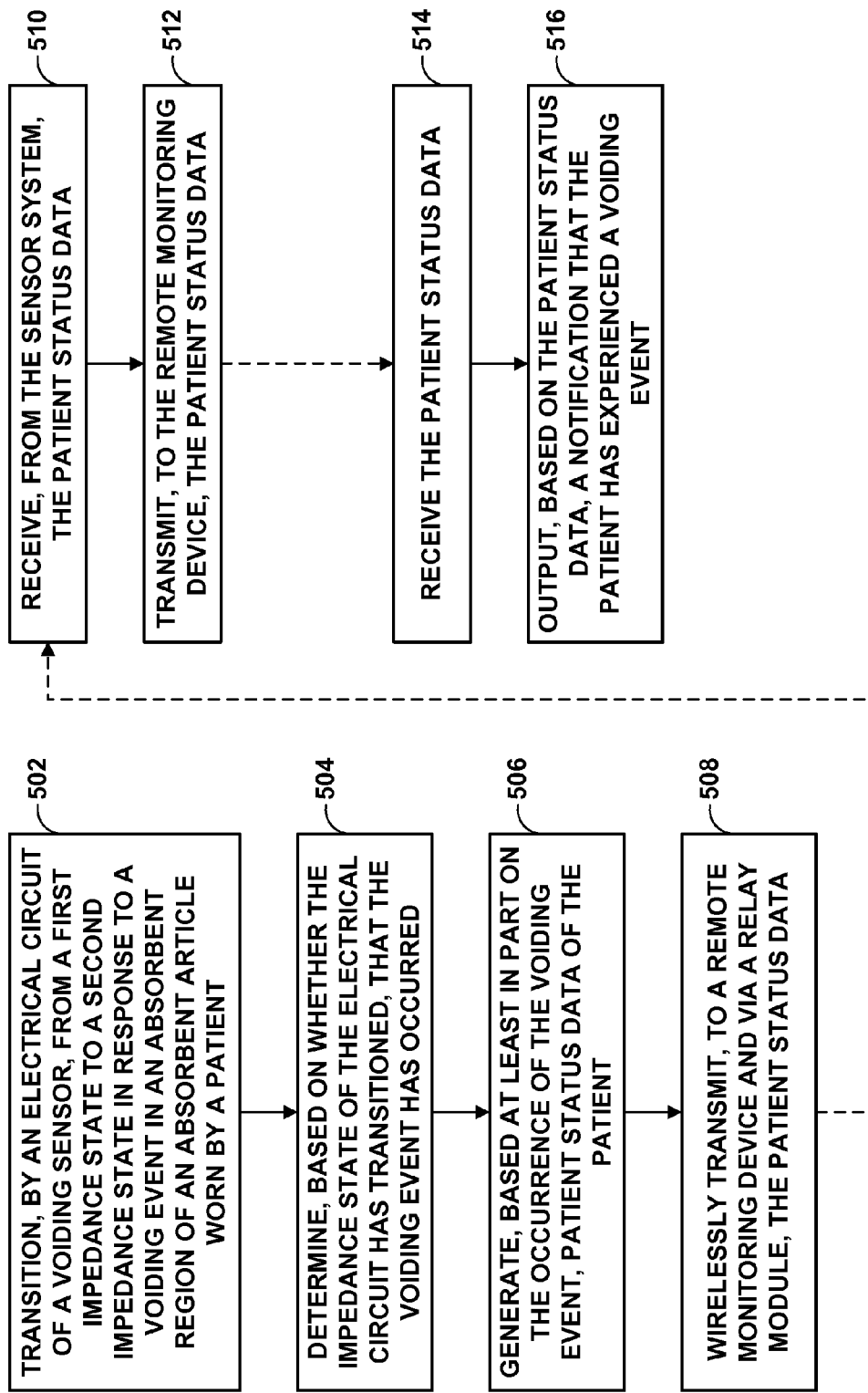
FIG. 5 is a flow diagram of an example technique for remotely monitoring the status of a patient, in accordance with one or more techniques of this disclosure.

FIG. 5 is a flow diagram of an example technique for remotely monitoring the status of a patient, in accordance with one or more techniques of this disclosure. For purposes of illustration, the techniques of FIG. 5 are described within the context of sensor system 6 of FIGS. 1 and 2, relay module 8 of FIGS. 1 and 3, and remote monitoring device 10 of FIGS. 1 and 4; devices having configurations different than that of sensor system 6, relay module 8, and remote monitoring device 10 may perform the techniques of FIG. 10.

As discussed above, a patent with urinary incontinence may wear an absorbent article, such as absorbent article 4 of FIG. 1. The patient may experience a voiding event (e.g., the patient may emit urine into absorbent region 12 of the absorbent article 4. In accordance with one or more techniques of this disclosure, sensor system 6 may detect the occurrence of the voiding event. For example, electrical circuit 32 of voiding sensor 20 of sensor system 6 may transition from a first impedance state to a second impedance state in response to the voiding event (502) and sensor system 6 may determine, based on whether the impedance state of electrical circuit 32 has transitioned, that the voiding event has occurred (504). In some examples, as discussed below, processors 22 of sensor system 6 may execute voiding detection module 42 to determine whether the impedance state of electrical circuit 32 has transitioned based on a voltage across a sense resistor, such as resistor 40.

As one example, where electrical circuit 32 is open in the first impedance state, a current path may not be present between first electrically conductive pathway 36 and second electrically conductive pathway 38. Without a current path between first electrically conductive pathway 36 and second electrically conductive pathway 38, current supplied by voltage source 34 may not flow through resistor 40, which may cause the voltage drop across resistor 40 to be approximately zero. Where the voltage drop across resistor 40 is approximately zero, processors 22 may determine that the impedance state of electrical circuit 32 is open.

In this example, electric circuit 32 may transition from open to closed in response to a voiding event. For instance, first electrically conductive pathway 36 and second electrically conductive pathway 38 may include an electrically conductive ink and/or an electrically conductive wire configured such that current may flow between first electrically conductive pathway 36 and second electrically conductive pathway 38 when a conductive fluid is present (e.g., in response to the voiding event) in absorbent region 12. With such a current path between first electrically conductive pathway 36 and second electrically conductive pathway 38, current supplied by voltage source 34 may flow through resistor 40, which may cause the voltage drop across resistor 40 to be greater than zero. Where the voltage drop across resistor 40 is greater than zero, processors 22 may determine that the impedance state of electrical circuit 32 is closed. In this way, electrical circuit 32 may be configured to transition from open to closed in response to a voiding event, and processors 22 may be configured to determine that electrical circuit 32 transitioned from a first impedance state to a second impedance state.

While described above as transitioning from open to closed in response to a voiding event, electrical circuit 32 may alternatively be configured to transition from closed to open in response to a voiding event. For instance, first electrically conductive pathway 36 and second electrically conductive pathway 38 may be coupled by an electrically conductive material configured to conduct current between first electrically conductive pathway 36 and second electrically conductive pathway 38. As discussed above, with such a current path between first electrically conductive pathway 36 and second electrically conductive pathway 38, current supplied by voltage source 34 may flow through resistor 40, which may cause the voltage drop across resistor 40 to be greater than zero such that processors 22 may determine that the impedance state of electrical circuit 32 is closed. However, in this example, the electrically conductive material (e.g., a silver salt) may be configured to at least partially dissolve in the presence of voiding fluid (i.e., in response to the voiding event), such that a current path is no longer present between first electrically conductive pathway 36 and second electrically conductive pathway 38. Without a current path between first electrically conductive pathway 36 and second electrically conductive pathway 38, current supplied by voltage source 34 may not flow through resistor 40, which may cause the voltage drop across resistor 40 to be approximately zero. Where the voltage drop across resistor 40 is approximately zero, processors 22 may determine that the impedance state of electrical circuit 32 is open. In this way, electrical circuit 32 may be configured to transition from closed to open in response to a voiding event, and processors 22 may be configured to determine that electrical circuit 32 transitioned from a first impedance state to a second impedance state.

In any case, sensor system 6 may generate, based at least in part on the occurrence of the voiding event, patient status data of the patient (506). For instance, processors 22 may execute patient status module 46 to generate patient status data that indicates the occurrence of a voiding event.

Sensor system 6 may wirelessly transmit, to a remote monitoring device and via a relay module, the patient status data (508). For example, processors 22 may cause communication module 24 to transmit the patient status data to relay module 8 using a low-power transmission method, such as ZigBee.

In some examples, in addition to or in place of determining whether a voiding event has occurred, sensor system 6 may determine whether a patient is attempting to use a conventional bathroom. For instance, motion sensors 28 may generate motion data that indicates patient motion and/or posture state of the patient. Processors 22 may execute motion detection module 44 to analyze the detected motions and/or posture states to determine whether the patient is moving in a manner associated with an attempt to use a conventional bathroom. For instance, motion detection module 44 may analyze the motion data to determine whether an activity level of the patient satisfies an activity level threshold. Motion detection module 44 may output an indication that the patient is attempting to use a conventional bathroom to patient status module 46, which may determine patient status data based on the indication. Patient status module 46 may cause communication module 24 to transmit the patient status data to relay module 8.

In some examples, motion detection module 44 may refrain to may cause communication module 24 to transmit the patient status data during certain times of day. For example, motion detection module 44 may only cause communication module 24 to transmit the patient status data during a particular time period (e.g., between the hours of 1 am and 4 am). The particular time period may be selected based on fall injury rates. For instance, after going to sleep, a patient may not generate enough urine to require voiding until approximately 1am to approximately 4 am. In this way, motion detection module 44 may reduce the number of "false positive" indications that the patient is attempting to use a conventional bathroom.

In any case, relay module 8 may receive the patient status data from sensor system 6 (510). For instance, processors 50 of relay module 8 may receive the patient status data via receiver 52 of relay module 8. Relay module 8 may forward the received patient status data to remote monitoring device 10. For instance, processors 50 may execute forwarding module 46, which may cause one or more of transmitters 54 to transmit the patient status data to remote monitoring device 10. In some examples, a first transmitter of transmitters 54 may be configured to transmit the patient status data over an internet-accessible wireless communications network. For instance, the first transmitter of transmitters 54 may be configured to transmit the patient status data to a hardwired network switch, a Wi-Fi access point or a Cellular base station, any of which may send the patient status data to a server, which may forward the patient status data to remote monitoring device 10. In some examples, a second transmitter of transmitters 54 may be configured to transmit the patient status data using the same protocol as receiver 52. For instance, where receiver 52 receives the patient status data using a wireless relay network protocol (e.g., ZigBee), the second transmitter of transmitters 54 may be configured to transmit the patient status data to remote monitoring device 10 using the same wireless relay network protocol. In this way, relay module 8 may receive and transmit the patient status data using the same wireless relay network.

Where transmitters 54 include different types of transmitters (e.g., the first transmitter and the second transmitter discussed above), forwarding module 46 may select a transmitter of transmitters 54 to transmit the patient status data. In some examples, the transmitter selection may be determined based on configuration settings stored by memory 56.

In any case, remote monitoring device 10 may receive the patient status data (514). For instance, processors 60 of remote monitoring device 10 may receive the patient status data via receiver 62 of remote monitoring device 10. In some examples, remote monitoring device 10 may receive the patient status data directly from relay module 8. In some examples, such as where relay module 8 transmits the patient status data to a server, remote monitoring device 10 may receive the patient status data from the server.

Remote monitoring module 10 may output, based on the patient status data, one or more notifications. For instance, processors 60 may execute patient monitoring module 70 to output the one or more notifications. As one example, processors 60 may execute patient monitoring module 70 to output a notification, via UI 66, that the patient has experienced a voiding event (516). In this way, a caregiver may determine whether a patient has experienced a voiding event without manually checking the patient's absorbent article. This may enable the caretaker to monitor a plurality of patients in an efficient manner, as well as enable patient monitoring without intruding in the patient's personal space.

As another example, processors 60 may execute patient monitoring module 70 to output a notification that the patient is attempting to use a conventional bathroom. In this way, a caretaker may be notified that a patient is attempting to use a conventional bathroom such that the caretaker may assist the patient, which may prevent injuries due to falling.

Figure 6A:
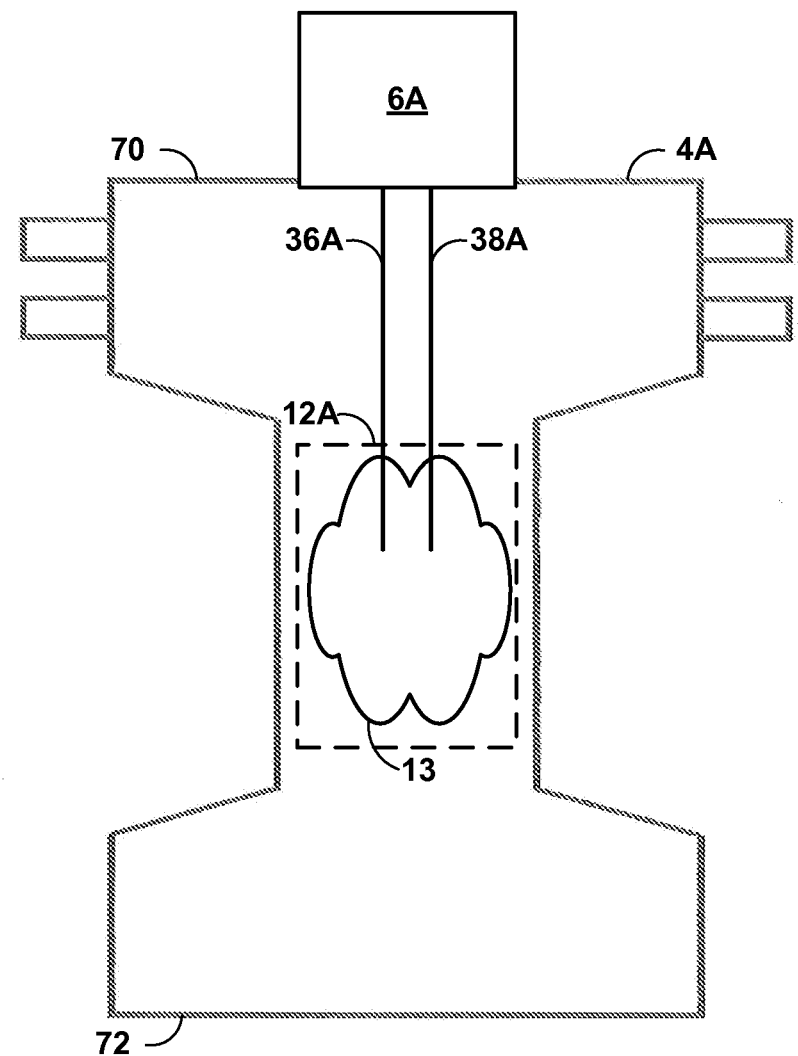
FIGS. 6A-6C illustrate various example configurations of sensor systems and absorbent articles, in accordance with one or more techniques of this disclosure.
Figure 6B:
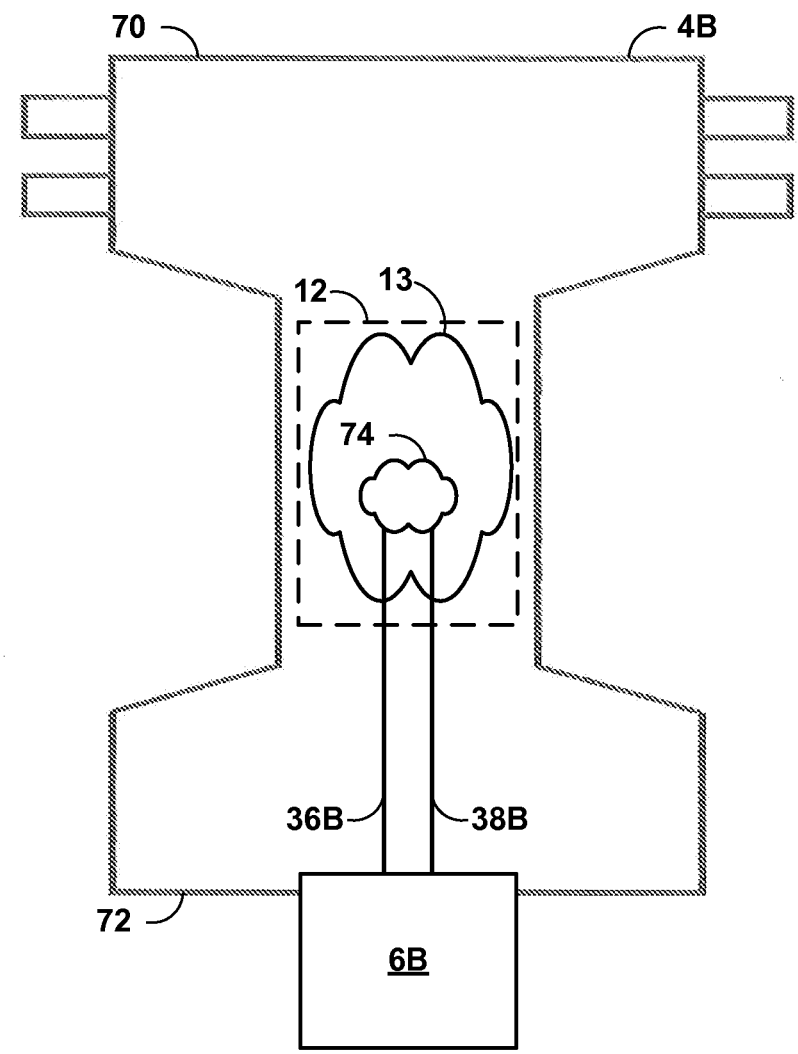
Figure 6C:
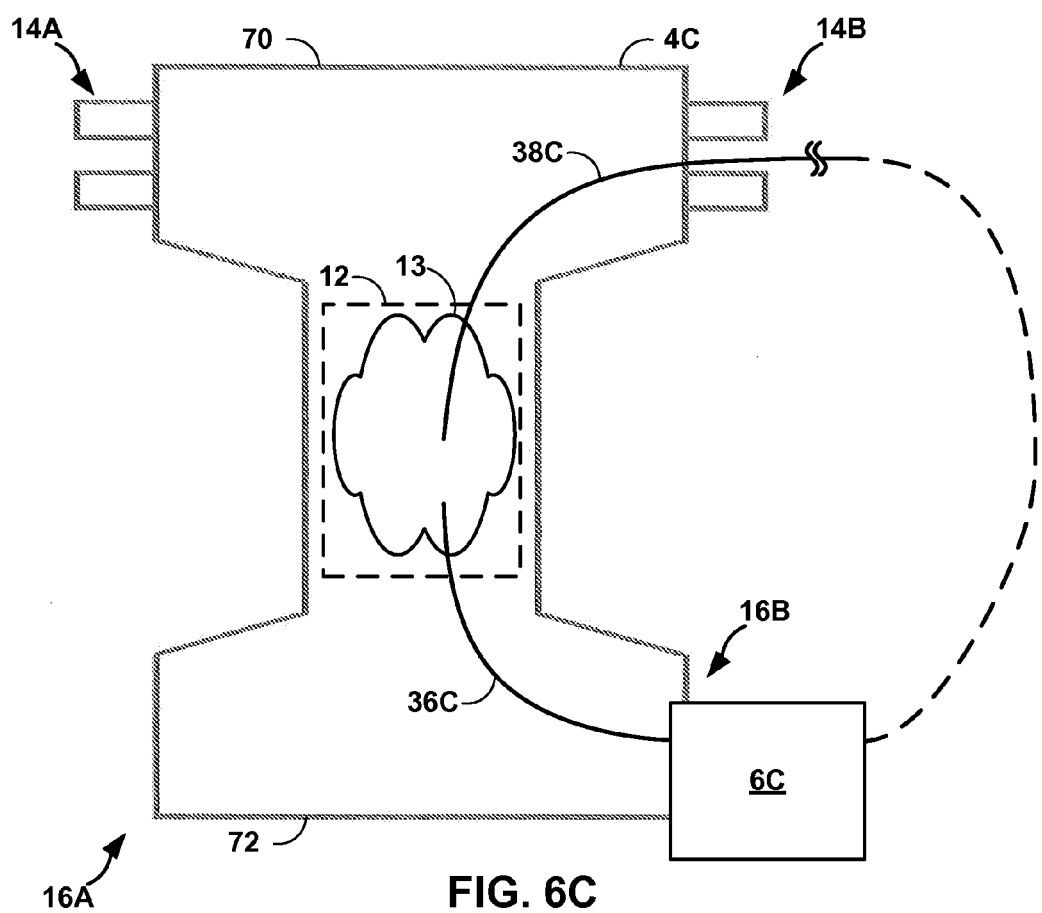

FIGS. 6A-6C each illustrates an example configuration of a sensor system and an absorbent article, in accordance with one or more techniques of this disclosure. As illustrated in FIG. 6A, sensor system 6A may be attached to side 70 of absorbent article 4A and first electrically conductive pathway 36A second electrically conductive pathway 38A may extend from sensor system 6A into absorbent region 12A of absorbent article 4A.

As discussed above, voiding sensor 20 (FIG. 2) may include electrical circuit 32 which may be configured to transition from a first impedance state to a second impedance state in response to a voiding event. FIG. 6A illustrates the example where the first impedance state is open and the second impedance state is closed. In the example of FIG. 6A, when voiding fluid 13 is not present, there may not be a current path between first electrically conductive pathway 36A second electrically conductive pathway 38A. However, the presence of voiding fluid 13 may create a current path that enables current to flow between first electrically conductive pathway 36A second electrically conductive pathway 38A.

As illustrated in FIG. 6B, sensor system 6B may be attached to second side 72 of absorbent article 4B and first electrically conductive pathway 36B second electrically conductive pathway 38B may extend from sensor system 6B into absorbent region 12B of absorbent article 4B. FIG. 6B illustrates the example where the first impedance state is closed and the second impedance state is open. In the example of FIG. 6B, when voiding fluid 13 is not present, electrically conductive material 74 may create a current path that enable current to flow between first electrically conductive pathway 36B second electrically conductive pathway 38B. However, the presence of voiding fluid 13 may remote this current path such that current does not flow between first electrically conductive pathway 36B second electrically conductive pathway 38B. For instance, electrically conductive material 74 may be configured to at least partially dissolve in the presence of voiding fluid 13.

As illustrated in FIG. 6C, sensor system 6C may be attached to second side 72 of absorbent article 4C and first electrically conductive pathway 36C may extend from sensor system 6C into absorbent region 12C of absorbent article 4C. As also illustrated in FIG. 6C, second electrically conductive pathway 36C may extend from absorbent region 12C and connect to sensor system 6C when absorbent article 4C is worn by a patient. For instance, when straps 14A and 14B are respectively attached to strap receiving regions 16A and 16B, second conductive pathway 36C may be attached (or may become attachable to) sensor system 6C.

The features shown in FIGS. 6A-6C may be used in any combination. For instance, sensor system 6 may be attached to or included anywhere in absorbent article 4 (e.g., attached proximate to first edge 70, second edge 72, or anywhere else on or in absorbent article 4). Additionally, the first impedance state being open or closed is not dependent on the placement of sensor system 6. For instance, in the example of FIG. 6A sensor system 6A is attached proximate to first edge 70 and the first impedance state is open, however, in other examples, sensor system 6 may be attached proximate to first edge 70 and the first impedance state may be closed (e.g., the absorbent article may include electrically conductive material 74).

The techniques described in this disclosure may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as clinician or patient programmers, medical devices, or other devices.

In one or more examples, the functions described in this disclosure may be implemented in hardware, software, firmware, or any combination thereof. If implemented in software, the functions may be stored, as one or more instructions or code, on a computer-readable medium and executed by a hardware-based processing unit. Computer-readable media may include computer-readable storage media forming a tangible, non-transitory medium. Instructions may be executed by one or more processors, such as one or more DSPs, ASICs, FPGAs, general purpose microprocessors, or other equivalent integrated or discrete logic circuitry. Accordingly, the term "processor," as used herein may refer to one or more of any of the foregoing structures or any other structure suitable for implementation of the techniques described herein.

In addition, in some aspects, the functionality described herein may be provided within dedicated hardware and/or software modules. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components. Also, the techniques could be fully implemented in one or more circuits or logic elements.

Various examples have been described. These and other examples are within the scope of the following claims.

What is claimed is:

1. A patient monitoring system comprising a sensor system, the sensor system comprising:
    a voiding sensor comprising an electrical circuit configured to be transitioned from a first impedance state to a second impedance state in response to a voiding event in an absorbent region of an absorbent article wearable by a patient, wherein the electrical circuit is either open or closed in the first impedance state and the other of open or closed in the second impedance state;
    one or more motion sensors configured to generate motion data indicative of motion of the patient;
    a communication module; and
    one or more processors configured to:
        determine, based on whether the impedance state of the electrical circuit is open or closed, that the voiding event has occurred,
        generate, based at least in part on the occurrence of the voiding event, first patient status data of the patient,
        cause the communication module to transmit, via a relay module and to a remote monitoring device that is distinct from the relay module, the first patient status data,
        determine, based at least in part on the motion data, patient motion or posture state,
        generate, based at least in part on the patient motion or posture state, second patient status data, and
        responsive to determining that a current time is within a predetermined time of day, cause the communication module to transmit, via the relay module and to the remote monitoring device, the second patient status data.

2. The system of claim 1, wherein the electrical circuit is open in the first impedance state and closed in the second impedance state.

3. The system of claim 2, wherein the electrical circuit comprises a first electrically conductive pathway and a second electrically conductive pathway configured to conduct in response to the voiding event such that the electrical circuit closes in response to the voiding event.

4. The system of claim 3, wherein the first and second electrically conductive pathways each comprise at least one of: an electrically conductive ink and an electrically conductive wire.

5. The system of claim 1, wherein the electrical circuit is closed in the first impedance state and open in the second impedance state.

6. The system of claim 5, wherein the electrical circuit comprises an electrically conductive pathway that comprises an electrically conductive material configured to at least partially dissolve in response to the voiding event such that the electrical circuit opens in response to the voiding event.

7. The system of claim 1, wherein the one or more processors are further configured to:
  determine, based on motion data, whether an activity level of the patient satisfies an activity level threshold, and
  cause the communication module to transmit, responsive to the activity level of the patient satisfying the activity level threshold, the second patient status data.

8. The system of claim 1, wherein the one or more processors are further configured to cause the communication module to transmit, responsive to the posture state being a sitting posture state or a standing posture state, the second patient status data.

9. The system of claim 1, wherein the one or more motion sensors comprise an accelerometer.

10. The system of claim 1, wherein the relay module comprises:
  a receiver configured to wirelessly receive, via a wireless relay network and from the sensor system, the first and second patient status data;
  a first transmitter configured to wirelessly transmit the first and second patient status data over an internet-accessible wireless communications network;
  a second transmitter configured to wirelessly transmit the first and second patient status data to a second wireless relay module over the wireless relay network; and
  one or more processors coupled to the first and second transmitters, the one or more processors being configured to select one of the first transmitter or the second transmitter for transmitting the received first and second patient status data.

11. The system of claim 10, wherein the receiver is configured to wirelessly receive the first and second patient status data over the wireless relay network from a plurality of sensor systems.

12. The system of claim 1, further comprising the absorbent article, wherein the voiding sensor is configured to be attached to the absorbent article.

13. A method of monitoring a patient status, the method comprising:
  transitioning, by an electrical circuit of a voiding sensor of a sensor system, from a first impedance state to a second impedance state in response to a voiding event in an absorbent region of an absorbent article worn by a patient, wherein the electrical circuit is either open or closed in the first impedance state and the other of open or closed in the second impedance state;
  determining, by one or more processors of the sensor system and based on whether the impedance state of the electrical circuit has transitioned, that the voiding event has occurred;
  generating, by the one or more processors and based at least in part on the occurrence of the voiding event, first patient status data of the patient;
  wirelessly transmitting, by a communication module of the sensor system and via a relay module that is distinct from the sensor system, the first patient status data to a remote monitoring device that is distinct from the relay module;
  determine, based at least in part on motion data generated by one or more motion sensors of the sensor system, patient motion or posture state, the motion data indicative of motion of the patient;
  generate, based at least in part on the patient motion or posture state, second patient status data; and
  responsive to determining that a current time is within a predetermined time of day, transmit, by the communication module and via the relay module, the second patient status data to the remote monitoring device.

14. The method of claim 13, wherein the electrical circuit is open in the first impedance state and closed in the second impedance state.

15. The method of claim 13, wherein the electrical circuit is closed in the first impedance state and open in the second impedance state.

16. The method of claim 13, further comprising:
  determining, based at least on the motion data, whether an activity level of the patient satisfies an activity level threshold; and
  wirelessly transmitting the second patient status data in response to the activity level of the patient satisfying the activity level threshold.

17. A non-transitory computer-readable storage medium storing instructions that, when executed, cause one or more processors of a sensor system to:
  determine, based on whether an impedance state of an electrical circuit of the sensor system has transitioned from a first impedance state to a second impedance state, that a voiding event has occurred, wherein the electrical circuit is configured to transition from the first impedance state to the second impedance state in response to the voiding event in an absorbent region of an absorbent article worn by a patient, and wherein the electrical circuit is either open or closed in the first impedance state and the other of open or closed in the second impedance state;
  generate, based at least in part on the occurrence of the voiding event, first patient status data of the patient;
  cause a communication module of the sensor system to wirelessly transmit, via a relay module that is distinct from the sensor system, the first patient status data to a remote monitoring device that is distinct from the relay module;
  determine, based at least in part on motion data generated by one or more motion sensors of the sensor system, patient motion or posture state, the motion data indicative of motion of the patient;
  generate, based at least in part on the patient motion or posture state, second patient status data; and
  responsive to determining that a current time is within a predetermined time of day, cause the communication module to transmit, via the relay module and to the remote monitoring device, the second patient status data.

18. A method of monitoring a status of a patient, the method comprising:
  receiving, by a remote monitoring device, from a sensor system, and via a relay module that is distinct from the remote monitoring device, first patient status data for the patient, wherein the sensor system is configured to identify a voiding event in an absorbent region of an absorbent article and includes:
    a voiding sensor comprising an electrical circuit configured to be transitioned from a first impedance state to a second impedance state in response to the voiding event in the absorbent region of the absorbent article,
    one or more motion sensors configured to generate motion data indicative of motion of the patient,
    a communication module,
    one or more processors configured to:
      determine, based on the second impedance state of the electrical circuit, that the voiding event has occurred, generate, based at least in part on the second impedance state, the first patient status data,
cause the communication module to wirelessly transmit, via the relay module and to the remote monitoring device, the first patient status data
determine, based at least in part on the motion data, patient motion or posture state,
generate, based at least in part on the patient motion or posture state, second patient status data, and
responsive to determining that a current time is within a predetermined time of day, cause the communication module to wirelessly transmit, via the relay module and to the remote monitoring device, the second patient status data; and in response to determining, based on the first patient status data, that the patient has experienced a voiding event, outputting, by the remote monitoring device, an indication that the patient has experienced a voiding event; and in response to receiving, by the remote monitoring device, the second patient status data, outputting an indication that the patient has gotten out of bed or is attempting to get out of bed.

19. The method of claim 18, further comprising:
receiving, by the remote monitoring device and via the relay module, patient status data for a plurality of respective patients, the patient status data for the plurality of patients being generated by a plurality of respective sensor systems, the patient status data including one or both of the first patient status data and the second patient status data.

20. The method of claim 19, wherein the plurality of patients is a first plurality of patients, wherein the plurality of sensor systems is a first plurality of sensor systems, and wherein the relay module is a first relay module, the method further comprising:
receiving, by the remote monitoring device and via a second relay module that is distinct from the remote monitoring device and the first relay module, patient status data for a second plurality of respective patients, the patient status data for the second plurality of patients being generated by a second plurality of respective sensor systems.

* * * * *